(12) United States Patent
Kolios et al.

(10) Patent No.: US 7,683,197 B2
(45) Date of Patent: Mar. 23, 2010

(54) INTEGRATED, CONTINUOUS METHOD FOR THE PRODUCTION OF MOLECULAR SINGLE-COMPONENT PERCURSORS HAVING A NITROGEN BRIDGING FUNCTION

(75) Inventors: Grigorios Kolios, Stuttgart (DE); Thomas Jäschke, Stuttgart (DE); Martin Jansen, Leonberg (DE)

(73) Assignee: Max-Planck-Gesellschaft zur Forderung der Wissenschaften EV, Munich (DE)

( * ) Notice: Subject to any disclaimer, the term of this patent is extended or adjusted under 35 U.S.C. 154(b) by 557 days.

(21) Appl. No.: 10/519,530

(22) PCT Filed: Jun. 27, 2003

(86) PCT No.: PCT/EP03/06853

§ 371 (c)(1),
(2), (4) Date: Apr. 29, 2005

(87) PCT Pub. No.: WO2004/002886

PCT Pub. Date: Jan. 8, 2004

(65) Prior Publication Data

US 2005/0202175 A1 Sep. 15, 2005

(30) Foreign Application Priority Data

Jun. 28, 2002 (DE) ................. 102 28 990

(51) Int. Cl.
*C07F 7/02* (2006.01)
(52) U.S. Cl. ............ 556/402; 556/410; 556/172; 556/173; 556/174; 556/176
(58) Field of Classification Search .............. 556/402, 556/410, 172, 173, 174, 176
See application file for complete search history.

(56) References Cited

U.S. PATENT DOCUMENTS

| 6,107,198 A | 8/2000 | Lin et al. |
| 2001/0000146 A1 | 4/2001 | Hwang et al. |

FOREIGN PATENT DOCUMENTS

| DE | 198 17 680 A | 10/1999 |
| DE | 100 45 428 A | 3/2002 |
| EP | 0 636 704 A | 2/1995 |

OTHER PUBLICATIONS

Database WPI, Section Ch, Week 199424, Derwent Publications Ltd., London, GB; AN 1994-196873 XP002263014 & JP 06 135715 A (Mitsubishi Materials Corp.), May 17, 1994) abstract.

*Primary Examiner*—Elvis O Price
(74) *Attorney, Agent, or Firm*—Sutherland Asbill & Brennan LLP

(57) ABSTRACT

The invention relates to a method for the regeneration of a reactor and the use of said method for the improved performance of production processes for desired products.

19 Claims, 3 Drawing Sheets

Figure 1:
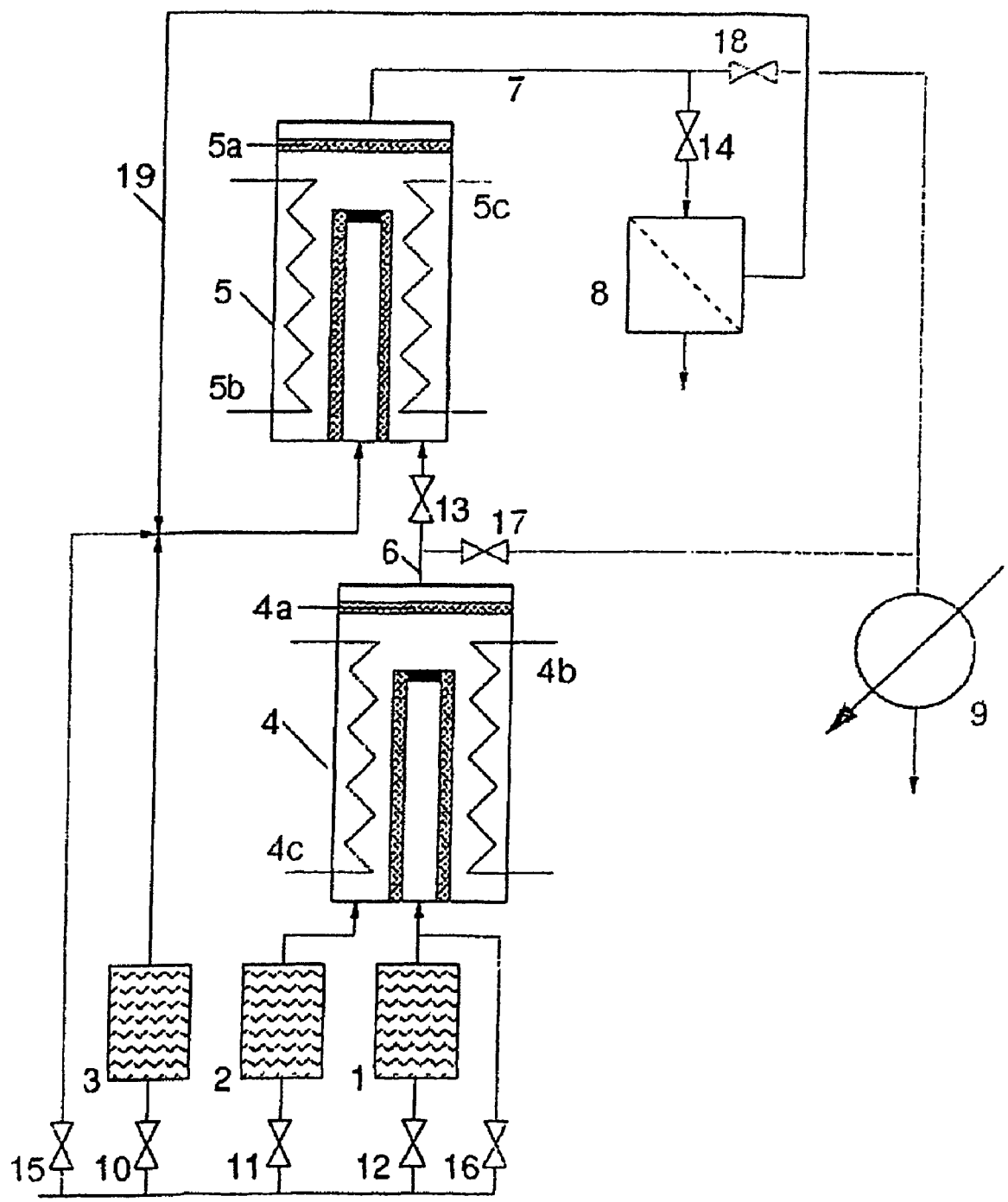

INTEGRATED, CONTINUOUS METHOD FOR THE PRODUCTION OF MOLECULAR SINGLE-COMPONENT PERCURSORS HAVING A NITROGEN BRIDGING FUNCTION

CROSS REFERENCE TO RELATED APPLICATIONS

This application claims the priority benefit of PCT/EP2003/006853 filed on Jun. 27, 2003 and German Application 102 28 990.5 filed on Jun. 28, 2002.

The invention relates to a method of regenerating a reactor and the use of this method for carrying out production processes for desired products in an improved manner.

The invention relates in particular to the realization of a continuous process for the preparation of molecular precursors for nonoxidic inorganic ceramics. Ceramics comprising the elements X, Y, N and C, where X and Y can be, for example, the elements Si, P, Al, Ti, V, Zr, Ta or B, are of particular interest. Ceramics of this type in which X=Si and Y=R have an extremely high thermal, mechanical and chemical stability. A prerequisite for these advantageous properties is the achievement of a regular sequence of X—N(—C)—Y bonds on an atomic scale. This prerequisite can be achieved by the synthesis and provision of a single-component precursor comprising the abovementioned elements and having a nitrogen bridging function. This precursor compound is subsequently polymerized and then, for example, ceramicized by pyrolysis to produce shaped bodies, fibers, films or coatings. The production of nonoxidic ceramics from molecular precursors makes it possible to obtain materials which have a very high purity. Furthermore, such single-component precursors ensure a homogeneous distribution of the participating elements in the ceramic.

A process for the subsystem SiBNC is described in EP 0 502 399 A2. The required single-component precursor TADB is, according to this publication, synthesized in a two-stage liquid-phase process in the batch mode. An industrial process having the above-described features has been realized by Bayer AG on the pilot plant scale.

A breakthrough in the production of nonoxidic inorganic ceramics has been achieved by the discovery of a synthetic route starting from volatile starting materials in DE 100 45 428 A1. This route has made it possible for the first time to prepare dichloroborylmethyltrichlorosilylamine (DMTA), the single-component precursor for an SiNCB ceramic in the gas phase.

While the process proposed there gives excellent results, further improvements are desirable from an industrial point of view:
1. The synthesis of the single-component precursor according to DE 100 45 428 is carried out in a two-stage reaction process whose reaction steps are carried out sequentially in time. The intermediate from the first reaction step usually has to be stored in a solvent at low temperatures, since it would polymerize rapidly at room temperature.
2. In the process described for the synthesis of DMTA, the by-product $MeNH_3Cl$ is formed as a solid in the first reaction step and the by-product $Cl_3SiNMeH_2Cl$ is formed as a solid in the second reaction step. It would be desirable to suppress the accumulation of these substances in the process. In industrial implementation of the process of DE 100 45 428 A1 in a batch or semibatch procedure with regular discharge of the by-products from the reaction volume, oxygen and moisture from the surrounding air can contaminate the reaction space, which would seriously impair the product quality. This would make costly purging of the entire plant before each production procedure necessary.
3. Large excesses of valuable starting materials have hitherto been necessary, and the cost of these has an adverse effect on the economics of the process. It would be desirable to minimize the excess required or to recirculate the excess starting materials to the process.

It was therefore an object of the present invention to provide an effective process which can be used for the entire class of substances specified at the outset and should, in particular, conform to the following aspects:
  The process should be able to be carried out continuously or pseudocontinuously without the reaction space being brought into contact with the surrounding air.
  The product yield should be optimized by minimizing the stoichiometric excess of starting materials and maximizing the selectivity with which the product is separated off.
  Excess starting materials and valuable intermediates should be able to be recirculated to the process.

This object is achieved, according to the invention, by the methods/processes specified in the claims.

The invention relates in particular to a temperature-driven cyclic procedure in an assembly of flow apparatuses. The invention is based on the observation that the ammonium salts formed in a reaction, in particular in the two reaction steps, decompose at moderate temperatures (<200° C.) to form volatile substances. From this, we have derived an elegant way of driving these substances out of the reaction volume purely thermally.

Accordingly, the invention provides, in a first aspect, a method of regenerating a reactor, in which ammonium salts formed as by-product in the reactor are brought into the gas phase at temperatures of $\geq 150°$ C., in particular $\geq 180°$ C. and more preferably at $\geq 200°$ C., and up to 1000° C., preferably up to 600° C., more preferably up to 400° C. and most preferably up to 300° C. It has surprisingly been found that the ammonium salts formed in many reactions, in particular in reactions for preparing single-component precursors of nonoxidic ceramics, can be sublimed at these temperatures and thus brought into the gas phase. These ammonium salts, which normally precipitate in the production of the desired substances and accumulate in the reactor, can thus be driven from the reactor in gaseous form in a simple manner without opening of the reactor for mechanical removal of solid substances being necessary.

The regeneration step according to the invention can be used, in particular, in the process for preparing a desired product in which ammonium salt is formed as by-product. While it has hitherto been necessary in such processes to remove the solid ammonium salt, the undesirable by-products can be removed from the reactor and, if appropriate, separated off in a simple fashion by means of the thermal regeneration step disclosed herein.

The regeneration step of the invention is particularly preferably used in a process for preparing single-component precursors of nonoxidic ceramics, which have a nitrogen bridging function. The synthesis of the single-component precursor is preferably carried out in the gas phase in a two-stage reaction process. The synthesis phase and the regeneration phase, i.e. the discharge of hardly volatile by-products by thermal treatment of the reactor, are preferably carried out cyclically in succession, with one cycle consisting of a production phase and a regeneration phase. The production phases and regeneration phases can be of the same or different duration and generally encompass a time span of from 10 seconds to 24 hours, in particular from 1 minute to 10 hours.

Switching over between the production phase and the regeneration phase can take place in a time-controlled or state-controlled fashion, advantageously in accordance with the total pressure drop in the reaction steps at intervals ranging from 10 seconds to 24 hours.

The process of the invention can, in particular, be used for preparing compounds which have the structural feature X—N—Y and in particular the structural feature X—N(—C)—Y, where X and Y are each, independently of one another, Si, P, Al, Ti, V, Zr, Ta, B, Ga or In. It is particularly preferably used for preparing a compound having the formula (I)

where the radicals Hal are each, independently of one another, Cl, Br or I, the radicals R are each, independently of one another, a hydrocarbon radical having from 1 to 20 carbon atoms or hydrogen, $R^1$ is a hydrocarbon radical having from 1 to 20 carbon atoms or hydrogen, x is 0, 1 or 2 and y is 0 or 1.

The desired products are preferably prepared in a two-stage process. The compounds of the formula (I) are, for example, prepared by reacting an amine component $R^1NH_2$ successively with a silane component $SiHal_{4-x}R_x$ and a borane component $BHal_{3-y}R_y$ in any order.

Preference is given to reacting the silane component in the gas phase with the amine component in the first step, continuously or in portions, with or without carrier gas. In the second step the intermediate formed is in turn preferably reacted further with the borane component in the condensed phase, in an inert solvent or preferably in the gas phase.

This reaction route can be used to prepare, inter alia, the compound dichloroborylmethyltrichlorosilylamine $Cl_3Si$—$N(CH_3)$—$BCl_2$ (DMTA) in pure form. Here, tetrachlorosilane and methylamine are firstly reacted in the gas phase. Methyltrichlorosilylamine is formed as intermediate and is reacted in condensed form or preferably the gas phase with trichloroborane.

In the formula (I), the radicals R and $R^1$ can each be, independently of one another, a hydrocarbon radical having from 1 to 20 carbon atoms, preferably from 1 to 10 carbon atoms. A hydrocarbon radical is a radical formed by the elements carbon and hydrogen. According to the invention, the hydrocarbon radical can be branched or unbranched, saturated or unsaturated. The hydrocarbon radical can also comprise aromatic groups which may in turn be substituted by hydrocarbon radicals. Examples of preferred hydrocarbon radicals are unbranched saturated hydrocarbon radicals such as $C_1$-$C_{20}$-alkyl, in particular methyl, ethyl, n-propyl, n-butyl, n-pentyl, n-hexyl, n-heptyl, n-octyl, n-nonyl and n-decyl. However, the radicals R can also be branched saturated hydrocarbons, in particular branched $C_3$-$C_{20}$alkyls such as i-propyl, i-butyl, t-butyl and further branched alkyl radicals. In a further, preferred embodiment, the radical R has one or more olefinically unsaturated groups. Examples of such radicals are vinyl, allyl, butenyl, pentenyl, hexenyl, heptenyl, octenyl, nonenyl, decenyl, butadienyl, pentadienyl, hexadienyl, heptadienyl, octadienyl, nonadienyl and decadienyl. The radical R can also contain an alkyne group, i.e. a C≡C bond. In a further, preferred embodiment, at least one radical R and preferably all radicals R comprise(s) an aromatic group, in particular an aromatic group having from 5 to 10 carbon atoms, in particular 5 or 6 carbon atoms, for example a phenyl group or an aromatic group, in particular phenyl group, substituted by a hydrocarbon, in particular a $C_1$-$C_{10}$-hydrocarbon, for example methylphenyl, dimethylphenyl, trimethylphenyl, ethylphenyl or propylphenyl. Including the substituents, the aromatic radical preferably has from 5 to 20, in particular up to 10, carbon atoms. The hydrocarbon radicals R and $R^1$ can each be varied independently of one another.

Particular preference is given to at least one radical R or/and $R^1$ and in particular all radicals R and/or $R^1$ comprising a $C_1$-$C_{20}$-alkyl group, in particular a $C_1$-$C_6$-alkyl group, a phenyl group, a vinyl group or an allyl group or a hydrocarbon radical having from 1 to 3 carbon atoms, in particular methyl, ethyl or propyl and most preferably methyl.

The radical Hal is a halogen atom and is in particular Cl, Br or I, with preference being given to at least one radical Hal and preferably all radicals Hal being Cl.

According to the invention, a cycle is divided into two phases: in the first phase, which is in the present text also referred to as synthesis phase or production phase, the desired product, e.g. a single-component precursor, is synthesized and isolated in pure form. Excess starting materials are recirculated to the synthesis process. In the second phase of the cycle, which is in the present text referred to as regeneration phase, the ammonium salts formed in the first and second reaction steps are thermally decomposed and discharged from the reaction volume. Valuable components can be completely or partly isolated and recirculated to the synthesis process.

The switching over between the production phase and the regeneration phase can be initiated externally or can advantageously be controlled by the total pressure drop in the reaction steps.

According to the invention, reaction products formed in solid form in the reaction during the production phase are preferably retained in the reaction volume by means of porous filters, in particular in both reaction steps, while gaseous components of the reaction mixture are passed on. They can, for example, be passed on by forced convection.

The solid by-products which are retained in the reaction volume are thermally brought into the gas phase, for example by sublimation, vaporization or thermal decomposition, during the regeneration phase and can then be discharged in gaseous form from the reaction volume without problems. The ammonium salts can be discharged undiluted or in an inert carrier gas stream.

The change between production phase and regeneration phase can also be achieved by means of a change in the temperature of the heat transfer medium provided for thermostatting the reactors. To regulate the temperature of the reaction steps, it is possible to use identical or different heat transfer media in the reaction steps and during the production or regeneration phase.

In a particularly advantageous embodiment of the invention, pseudocontinuous production of the product, for example DMTA, is realized. For this purpose, the two-stage (or multistage) reaction is carried out using two apparatuses per reaction step, of which one apparatus is operated in the production mode and the other apparatus is operated in the regeneration mode. As a result of appropriate switching over, one of the stages is always in the production mode and one of the stages in the regeneration mode, so that continuous production and at the same time regeneration is achieved.

The desired target product is advantageously isolated from the other components of the reaction mixture obtained from the last reactor, for example by crystallization, condensation or by the use of solvents such as hexane. However, it is also possible to carry out the isolation of the target product without using a solvent. The isolation of the target product is preferably carried out continuously.

The procedure according to the invention, in particular the transfer of solid by-products into the gas phase, allows undesirable by-products to be separated off and, in addition, valuable starting materials or intermediates present therein to be recirculated to the process after the separation step for separating off the desired product or the undesirable by-products. Unreacted starting materials are advantageously fed as feed stream into the second reaction step.

As starting materials for the first reaction step, use is advantageously made of $MeNH_2$ and at least one of the compounds $SiCl_4$, $BCl_3$, $PCl_3$, $PCl_5$, $AlCl_3$, $GaCl_3$, $InCl_3$, $TiCl_4$, $VCl_3$, $VCl_4$, $ZrCl_4$ or $TaCl_5$. As starting materials for the second reaction step, use is advantageously made of the intermediate from the first reaction step and at least one of the compounds $SiCl_4$, $BCl_3$, $PCl_3$, $PCl_5$, $AlCl_3$, $GaCl_3$, $InCl_3$, $TiCl_4$, $VCl_3$, $VCl_4$, $ZrCl_4$ or $TaCl_5$. In addition, recycled starting materials or intermediates can be used.

The cycle consisting of production phase and regeneration phase is preferably carried out at least once, in particular at least twice and particularly preferably at least five times, in the processes of the invention.

The invention is illustrated by the accompanying FIGS. 1 to 4 and the following examples.

FIG. 1 schematically shows the production phase in a two-stage process.

Figure 2:
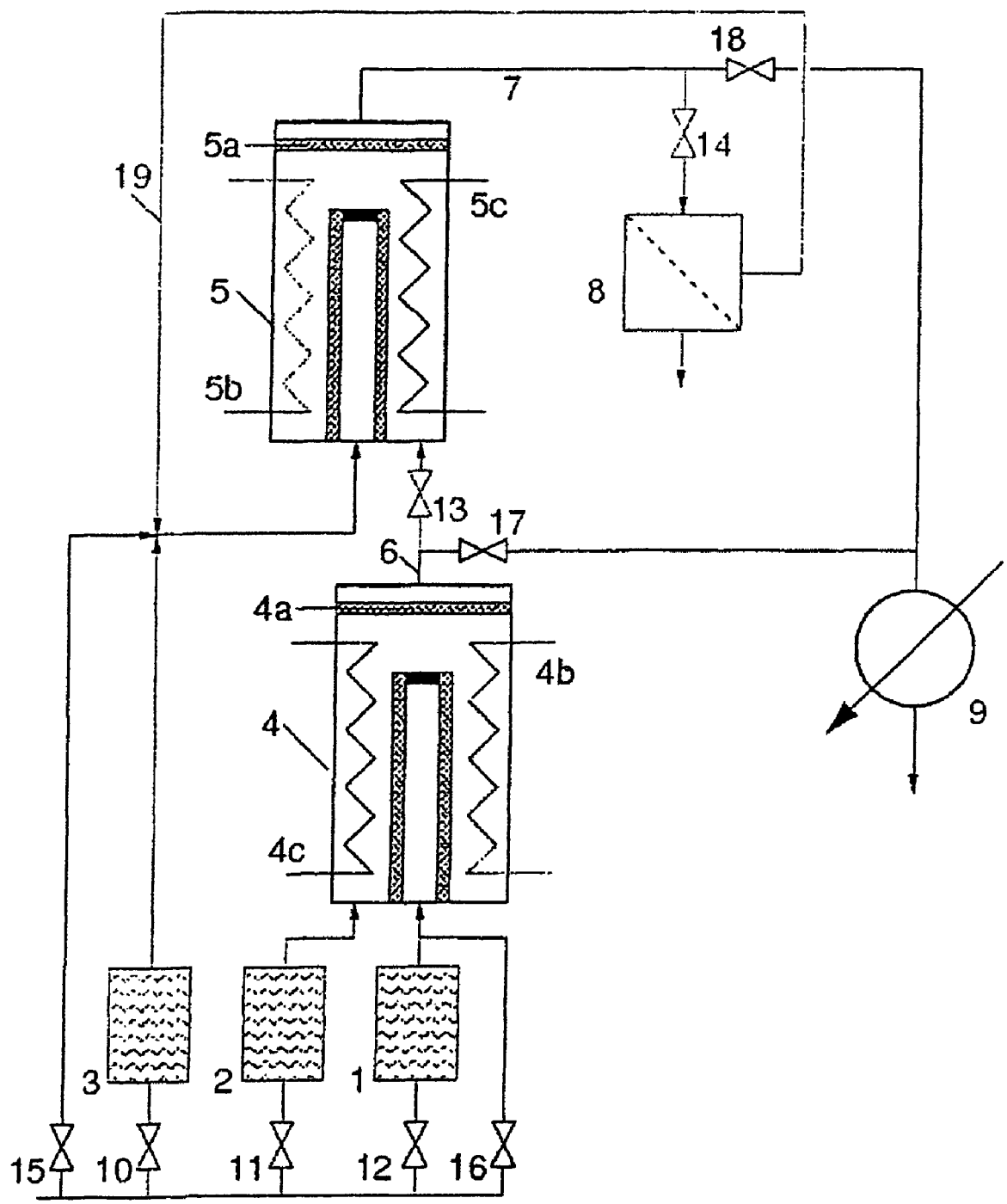

FIG. 2 schematically shows the regeneration phase in a two-stage process.

Figure 3:
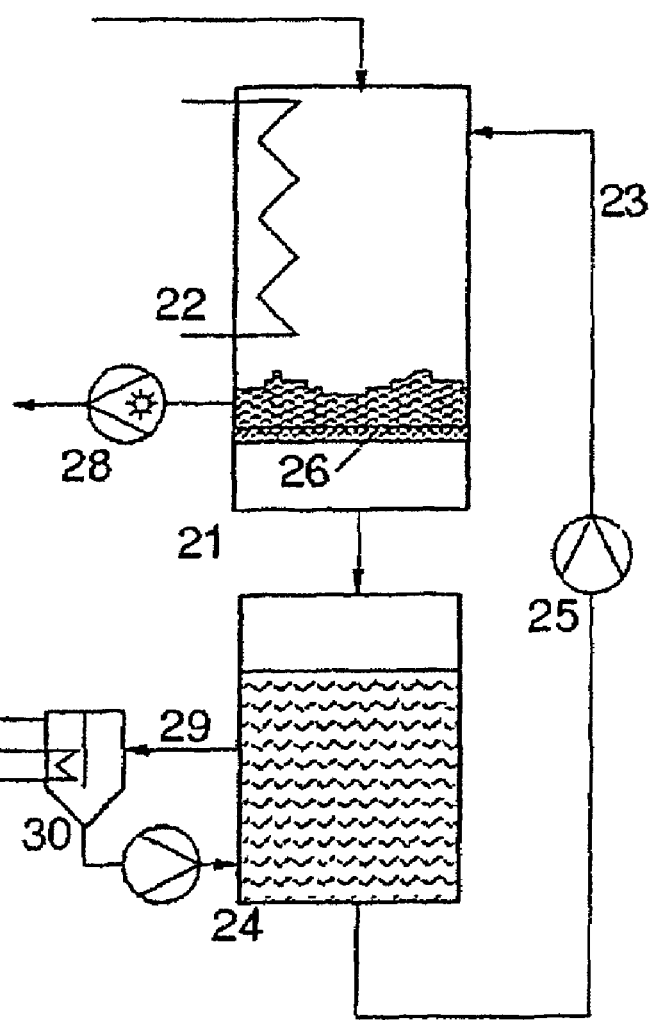
Figure 4:
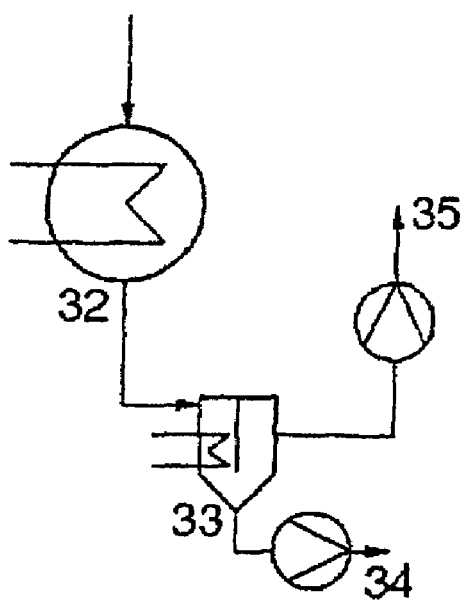

FIGS. 3 and 4 depict isolation steps for obtaining the pure end product and for obtaining recyclable process streams.

EXAMPLE 1

Synthesis of DMTA

FIG. 1 shows the process flow diagram according to an embodiment of the invention during the first phase of the cycle, hereinafter referred to as production phase.

During the production phase, the shutoff valves 10, 11, 12, 13, 14 are open and the shutoff valves 15, 16, 17, 18 are closed.

$MeNH_2$ from the thermostatted stock vessel 1 and $SiCl_4$ from the thermostatted stock vessel 2 are metered into the reactor 4 either in pure form or in an inert carrier gas stream, for example $N_2$, He, Ar, $CO_2$. The reactor temperature is regulated to a temperature in the range from −60° C. to +60° C. by means of an external heat transfer medium 4b. The total pressure in the reactor 4 is in the range from 1 mbar to 5 bar, and the residence time of the reaction mixture is in the range from 0.1 s to 10 s.

The starting materials are introduced together at one point or both distributed over different points or one at one point and one distributed over different points into the reactor of the first reaction step 4. During the production phase, preference is given to setting pronounced axial concentration profiles in the gas phase in the reaction steps. A stoichiometric excess of $SiCl_4$ over $MeNH_2$ of at least 2:1 is ensured in the overall reaction space by the manner of introduction and the flow conditions. The reaction takes place in the gas phase and the components of the reaction mixture which are gaseous at the reaction temperature set are taken off through an integrated filter 4a, while the ammonium salt which is present in solid form is retained in the reaction chamber.

The volatile components of the reaction mixture from the reactor 4 are conveyed in the line 6 which is thermostatted to a temperature in the range from −60° C. to +60° C. to the reactor 5. In addition, $BCl_3$ from the stock vessel 3 is introduced into the reactor 5, either in pure form or in an inert carrier gas stream, for example $N_2$, He, Ar, $CO_2$. The reactants are introduced both together at one point or both distributed over different points or one at one point and one distributed over different points into the reactor. A stoichiometric excess of $BCl_3$ over $Cl_3Si$—NMeH of at least 2:1 is ensured in the overall reaction space by the manner of introduction and the flow conditions. The reactor temperature is kept constant in the range from −60° C. to +120° C. by means of an external heat transfer medium 5b. The total pressure in the reactor 5 is in the range from 1 mbar to 5 bar, and the residence time of the reaction mixture is in the range from 0.1 s to 10 s. The reactor temperature is chosen so that the reaction to form DMTA occurs spontaneously. The components of the reaction mixture which are fluid at the reaction temperature are taken off from the reactor 5 through an integrated filter 5a and the solid reaction products are retained in the reactor. The reaction mixture taken off from the reactor 5 comprises the target product DMTA, excess $BCl_3$, any inert carrier gas used and possibly excess $SiCl_4$ and also traces of unreacted $MeNH_2$. The reaction mixture is conveyed in a thermostatted line 7, which is thermostatted to a temperature in the range from −60° C. to 120° C., to the separation stage 8. The separation stage for recovering the pure DMTA is described in detail below.

After a time in the range from 10 s to 24 h has elapsed, the second phase of the process is initiated under time control or state control. A suitable control parameter is, for example, the pressure difference between reactor inlet and reactor outlet. FIG. 2 shows the process flow diagram according to the invention during the second phase of the cycle, referred to as regeneration phase. During the regeneration phase, the shutoff valves 10, 11, 12, 13, 14 are closed and the shutoff valves 15, 16, 17, 18 are open. In this way, the stock vessels for the starting material $SiCl_4$, $MeNH_2$ and $BCl_3$ are closed off. Pure inert gas thus flows through the reactors. At the same time, the temperatures of the heat transfer media for thermostatting the reaction steps 4 and 5 are changed over.

The thermostatting of the reaction steps 4 and 5 can be carried out using one and the same heat transfer medium or using different heat transfer media.

During the regeneration phase, the temperatures of the reactors 4 and 5 are regulated to values above the sublimation temperature of the ammonium salts formed during the production phase. Temperatures in the range from 150° C. to 600° C., in particular from 200° C. to 400° C., are necessary for this. The inert carrier gas drives the volatile sublimation products from the reactors and regenerates them by removing the salt load which has accumulated during the production phase. As an alternative to the use of a carrier gas, the sublimation products can also be taken off by means of a vacuum pump.

The ammonium salts which have been discharged are recombined by cooling in the condenser 9 and are stored in a receiver.

After a time in the range from 10 s to 24 h has elapsed, the production phase as described above is initiated again either under time control or state control.

The process is continued by periodic switching between the production phase and the regeneration phase.

For continuous preparation of DMTA, a parallel arrangement of two reactors for the first reaction step and two reactors for the second reaction step is necessary. One reactor in each of the first and second reaction steps is operated in the production mode and one reactor in each of the first and second reaction steps is operated in the regeneration mode.

EXAMPLE 2

Isolation of DMTA

To isolate the target product DMTA from the reaction mixture, various separation methods can be used. The separation stage 8 is connected to the outlet of the second reaction step. The alternatives developed for the purposes of the invention are described below.

Product Isolation, Variant 1.

FIG. 3 schematically shows the separation stage described here.

The gaseous reaction mixture having the composition resulting from the reaction step 5 is introduced into a condenser 21. There, the condensable components of the reaction product are separated off from any carrier gas used. The condenser is cooled to a temperature in the range from −30° C. to +7° C. either indirectly (22) or directly (23) by means of a solvent, typically hexane. The solvent required is circulated from a stock vessel 24 by means of a pump 25. As a result of the circulation of the solvent, the DMTA concentration in the stock vessel increases to just below saturation. The DMTA which is additionally introduced with the reaction product therefore leads to supersaturation and precipitates in crystalline form. The suspension is filtered in the filter 26, so that DMTA is separated off as filter residue 27 from the other components of the reaction mixture. The crystalline DMTA can be discharged from the process by means of a cellular wheel pump 28 and either passed directly to polymerization or temporarily stored. $SiCl_4$, $BCl_3$ and $MeNH_2$, which can likewise be present in the product stream from the reaction step, are likewise soluble in hexane and are transported to the stock vessel. Heating of the second substream 29 which is conveyed continuously between the stock vessel 24 and the phase separator 30 enables $SiCl_4$, $BCl_3$ and $MeNH_2$, which are significantly more volatile than the solvent hexane, to be discharged from the process. To achieve this, the temperature in the phase separator 30 has to be in the range from +10° C. to 40° C. Since the stream 31 discharged typically comprises about 80-95% of $BCl_3$, about 4-20% of $SiCl_4$ and possibly traces of $MeNH_2$ and hexane, it can usefully be recirculated without after-treatment to the reaction step 5.

Product Separation, Variant 2.

The variant described here for separating off the product requires no solvent. The gaseous reaction mixture having the composition resulting from the reaction step 5 is introduced into a heat exchanger 32. The temperature is set to values in the range from 8° C. to 50° C. by means of a heat transfer medium, so that DMTA is obtained in liquid form and the partial pressures of the components $SiCl_4$, $BCl_3$ and $MeNH_2$ remain below their saturation vapor pressure. $SiCl_4$, $BCl_3$ and $MeNH_2$ and any carrier gas present are thus separated off from the condensed DMTA in the phase separator 33. The liquid DMTA 34 can either be passed directly to polymerization or be temporarily stored. The gas 35 discharged comprises the components $BCl_3$ and $SiCl_4$ in a volume ratio of from 5:1 to 20:1 and traces of $MeNH_2$ and also gaseous DMTA (<1000 ppm), possibly diluted with an inert carrier gas stream. This gas can usefully be recirculated without after-treatment to the reaction step 5.

The invention claimed is:

1. A cyclic process for preparing a single-component precursor of nonoxidic ceramic product, in which an ammonium salt is formed as a by-product in a reactor, comprising retaining the ammonium salt in the form of a precipitate in the reactor and thereafter bringing the ammonium salt from the precipitate into the gas phase by heating the reactor to a temperature of ≧150° C.

2. The process as claimed in claim 1, wherein the ammonium salt which has been brought into the gas phase is separated off.

3. The process as claimed in claim 1, wherein the product is a compound which has the structural feature X—N—Y, where X and Y can each comprise, independently of one another, Si, P, Al, Ti, V, Zr, B, Ga or/and In.

4. The process as claimed in claim 3, wherein the compound has the formula (I) $R_xHal_{3-x}Si-NR^1-BR_yHal_{2-y}$,
where the radicals Hal are each, independently of one another, Cl, Br or I,
the radicals R are each, independently of one another, a hydrocarbon radical having from 1 to 20 carbon atoms or hydrogen,
$R^1$ is a hydrocarbon radical having from 1 to 20 carbon atoms or hydrogen,
x is 0, 1 or 2 and
y is 0 or 1.

5. The process as claimed in claim 2, wherein the synthesis of the product, a single-component precursor, is carried out in a two-step reaction process.

6. The process as claimed in claim 2, wherein the process comprises the steps
(i) synthesizing the product, a single-component precursor of nonoxidic ceramics having a nitrogen bridging function, in a two-stage reaction and
(ii) regenerating the reactor by heating to temperatures of ≧150° C.

7. The process as claimed in claim 6, wherein the synthesis phase and the regeneration phase are carried out alternatively a plurality of times.

8. The process as claimed in claim 6, wherein the switching over between the synthesis phase and the regeneration phase is controlled by the total pressure drop in the reaction steps.

9. The process as claimed in claim 6, wherein the change between synthesis phase and regeneration phase is controlled by a temperature change.

10. A pseudocontinuous process for preparing a product, in which an ammonium salt is formed as by-product and the preparation is carried out in a two-stage reaction, comprising using two apparatuses per reaction stage, of which one is operated in the production mode and the other is operated in the regeneration mode at temperatures of ≧150° C.

11. The process as claimed in claim 10, wherein the product is isolated from the remaining components of the reaction mixture, in particular by crystallization, condensation and/or the use of a solvent.

12. The process as claimed in claim 10, wherein unreacted starting materials are recycled.

13. The process as claimed in claim 10, wherein $MeNH_2$ and at least one of the compounds $SiCl_4$, $BCl_3$, $PCl_3$, $PCl_5$, $AlCl_3$, $GaCl_3$, $InCl_3$, $TiCl_4$, $VCl_3$, $VCl_4$, $ZrCl_4$ or $TaCl_5$ are used as starting materials for the first reaction step.

14. The process as claimed in claim 10, wherein the intermediate product from the first reaction step and at least one of the compounds $SiCl_4$, $BCl_3$, $PCl_3$, $PCl_5$, $AlCl_3$, $GaCl_3$, $InCl_3$, $TiCl_4$, $VCl_3$, $VCl_4$, $ZrCl_4$ or $TaCl_5$ are used as starting materials for the second reaction step.

15. The process as claimed in claim 1, wherein the product is isolated from the remaining components of the reaction mixture, in particular by crystallization, condensation and/or the use of a solvent.

16. The process as claimed in claim 1, wherein unreacted starting materials are recycled.

17. The process as claimed in claim 5, wherein MeNH$_2$ and at least one of the compounds SiCl$_4$, BCl$_3$, PCl$_3$, PCl$_5$, AlCl$_3$, GaCl$_3$, InCl$_3$, TiCl$_4$, VCl$_3$, VCl$_4$, ZrCl$_4$, or TaCl$_5$ are used as starting materials for the first reaction step.

18. The process as claimed in claim 5, wherein the intermediate product from the first reaction step and at least one of the compounds SiCl$_4$, BCl$_3$, PCl$_3$, PCl$_5$, AlCl$_3$, GaCl$_3$, InCl$_3$, TiCl$_4$, VCl$_3$, VCl$_4$, ZrCl$_4$ or TaCl$_5$ are used as starting materials for the second reaction step.

19. The process as claimed in claim 6 wherein the synthesis phase and the regeneration phase are carried out cyclically in succession.

* * * * *